United States Patent
Harada et al.

(10) Patent No.: US 7,655,905 B2
(45) Date of Patent: Feb. 2, 2010

(54) CHARGED PARTICLE BEAM EQUIPMENT

(75) Inventors: Ken Harada, Wako (JP); Tetsuya Akashi, Fujimi (JP); Yoshihiko Togawa, Wako (JP); Tsuyoshi Matsuda, Wako (JP); Noboru Moriya, Wako (JP)

(73) Assignee: Riken, Saitama (JP)

( * ) Notice: Subject to any disclaimer, the term of this patent is extended or adjusted under 35 U.S.C. 154(b) by 256 days.

(21) Appl. No.: 11/920,132

(22) PCT Filed: May 11, 2006

(86) PCT No.: PCT/JP2006/309466

§ 371 (c)(1),
(2), (4) Date: Nov. 9, 2007

(87) PCT Pub. No.: WO2006/121108

PCT Pub. Date: Nov. 16, 2006

(65) Prior Publication Data

US 2009/0045339 A1 Feb. 19, 2009

(30) Foreign Application Priority Data

May 12, 2005 (JP) .............................. 2005-139495

(51) Int. Cl.
*G21K 5/10* (2006.01)
*G01N 23/00* (2006.01)
(52) U.S. Cl. .................. 250/306; 250/310; 250/311; 250/398; 250/397; 250/396 R; 250/492.2; 250/492.3; 250/442.11

(58) Field of Classification Search .............. 250/306, 250/310, 311, 398, 397, 396 R, 492.2, 492.3, 250/442.11
See application file for complete search history.

(56) References Cited

U.S. PATENT DOCUMENTS

| 6,444,991 | B1 | 9/2002 | Yamada et al. | |
| 7,071,475 | B2 * | 7/2006 | Tomimatsu et al. | .... 250/442.11 |
| 7,244,932 | B2 * | 7/2007 | Nakasuji et al. | ............. 250/306 |
| 7,439,502 | B2 * | 10/2008 | Nakasuji et al. | ............. 250/306 |

FOREIGN PATENT DOCUMENTS

| JP | 5-323859 | 12/1993 |
| JP | 8-153485 | 6/1996 |
| JP | 11-40097 | 2/1999 |
| JP | 2001-35433 | 2/2001 |

* cited by examiner

*Primary Examiner*—Nikita Wells
(74) *Attorney, Agent, or Firm*—Nixon & Vanderhye, P.C.

(57) ABSTRACT

Charged particle beam equipment having a rotary mechanism in which shift of the observing/machining position incident to the rotary operation of the equipment having the rotary mechanism can be corrected conveniently with high precision in a plane perpendicular to the optical axis of the optical system of charged particle beam or in a slightly inclining plane. An X-Y shift incident to rotation in a plane is determined from the angular information of a rotary mechanism such as a sample holder, diaphragms or biprisms in the charged particle beam equipment, and then driving or controlling is performed to cancel the X-Y shift.

24 Claims, 8 Drawing Sheets

CHARGED PARTICLE BEAM EQUIPMENT

This application is the U.S. national phase of International Application No. PCT/JP2006/309466 filed 11 May 2006 which designated the U.S. and claims priority to Japanese Application No. 2005-139495 filed 12 May 2005, the entire contents of each of which are hereby incorporated by reference.

TECHNICAL FIELD

The present invention relates to charged particle beam equipment, such as an electron microscope and ion beam machining equipment.

BACKGROUND ART

In the charged particle beam equipment, when performing observation or machining of a sample, it is necessary to set a position of the sample that is put under observation or to machining and positions of biprisms etc. in a situation preferable for observation or machining to an optical axis of a charged particle beam optical system. For this setting, a freedom of rotation of the charged particle beam in a plane on which the sample etc. is located may be required. Therefore, as a device having a mechanism that is rotatable in an XY plane perpendicular to the optical axis of the optical system of the charged particle beam or in a slightly inclining plane, rotary holders, such as a rotary holder in the electron microscope etc. and a rotary electron biprism holder in the electron beam holography microscope, have been put in practical use. When adjusting a position of the sample and positions of the biprism etc., the operator can adjust easily these rotary holders so that they may attain predetermined relations to the optical axis of the charged particle beam optical system by fine adjusting them in an X-axis direction and in a Y-axis direction (the optical axis of the optical system of the charged particle beam equipment is represented by a Z-axis) while viewing an observation screen.

However, when the adjustment of the position of the sample that is intended to be observed or machined and the adjustment of the position of the biprism etc. come with rotation, the adjustment is complicated. This is because it is normal to adjust the part that is intended to be observed and machined so that it may be disposed on the optical axis, and generally, this position does not agree with a rotation center of the rotary mechanism of the rotary holder. When any operation accompanied by a rotation is performed in this optical system, travels of attention-focused positions of the sample and the biprism occur in a rotation plane incident to this rotation operation, which results in a displacement of the position of the sample at which observation or machining is intended to be done and a displacement of the biprism etc. To correct this displacement, the displacement incident to the rotation operation is corrected by making it move in the X-axis direction and in the Y-axis direction in the XY plane so that the part in concern may not deviate from an observation view field or a machining position by visual observation each time the rotation operation of the sample holder or biprism holder is performed.

This correction operation accompanying this rotation operation is a time-consuming operation. Since the rotation operation itself is not a frequently performed operation in the charged particle beam equipment, there is no precedent where the rotation operation and the correction operation in an XY plane are controlled being connected to the each other. Therefore, currently this operation is recognized by the operator as an adjustment operation that the operator should perform naturally.

DISCLOSURE OF THE INVENTION

Problems to be Solved by the Invention

When the sample is intended to be observed or machined by a charged particle beam, if the position of the sample that needs to be observed or machined is simply shifted with respect to an optical axis, what is necessary is just to make the position in concern move in an X-axis direction and in a Y-axis direction in a plan perpendicular to the optical axis. However, if the electron beam holography is considered, the following situation will be understood very easily. For example, in the case where dust is adhered at a position that will be a path of a reference wave of the sample holder, simple movement in the X-axis direction and in the Y-axis direction does not allow a proper sample position to be chosen, rather an operation accompanying a rotation may be necessary. In this case, not only a correction operation in the X-axis direction and in the Y-axis direction incident to the rotation of the sample holder becomes necessary, but also, in some cases, a rotation operation becomes necessary for charged particle beam adjusting devices, such as other electron biprism, an objective aperture, and a selected area aperture, as will be described later.

Besides this case, in the case where the electron biprisms are used in multiple stages, as in "azimuth control of interference fringes by a two-stage electron biprism interference method" that is introduced in APPLIED PHYSICS LETTERS, Vol. 84, No. 17, 26 Apr. (2004) by the inventors of this application and is also disclosed in JP No. 2004-027274 by the inventors of this application, and in a "three-stage electron biprism interference method" disclosed in JP No. 2004-046633 by the inventors of this application, for example, the correction of the travel in the XY plane incident to the rotation operation described above becomes complex and needed to be done multiple times.

In light of the current situation, it is wished that the electron beam equipment be configured to be able to, when the operator performs a rotation operation, such as rotating the electron biprism, detect an instruction angle of the rotation operation or actually rotated angle and automatically perform correction in the XY plane that will becomes necessary with the rotation. Moreover, accompanying this, if rotation of other electron biprism(s) etc. is necessary or further if its correction is needed, it is desirable that the electron beam equipment is configured to be able to operate them in such a way that each of them is linked with the others.

Means for Solving the Problem

It is often the case that a sample holder, a variable diaphragm device, an electron biprism, etc. in the charged particle beam equipment recently developed and manufactured are each equipped with a two dimensional position sensitive detector and a driving part, such as a step motor, being mechanisms used by computer control. Paying attention to this respect, the present invention makes the equipment perform a necessary correction action of a position in the XY plane, by using a position sensitive detector and computer-controlled driving mechanism, further by utilizing an arithmetic capacity of the computer, so that a displacement incident to the rotation operation in the plane may be cancelled out. Moreover, by a single input a plurality of rotary mechanisms are made to be operated being mutually linked.

EFFECT OF THE INVENTION

According to the present invention, since it becomes unnecessary that the operator of the charged particle beam equipment makes equipment having a rotary mechanism, such as a rotary sample holder, act to cancel out the displacement incident to the rotation operation by complicated operations, an effect of improving operability and operation precision of the equipment having the rotary mechanism is produced.

BEST MODE FOR WORKING THE INVENTION

The present invention realizes an object that an image is inputted from the outside of a housing or from a position as close to a housing-side end part as possible with a minimum number of parts without impairing the thicknesses of constituents of an optical system.

First Embodiment

In the following, an explanation will be given, taking a sample holder as an example. However, explanation will be the same for equipment having other rotary mechanism.

FIGS. 1A to 1C are diagrams for explaining a rotation operation of a sample holder and a correction operation that becomes necessary incident to this. A reference numeral 10 is a sample holder. The sample holder 10 consists of a holder plate 1 and a rotatable sample hold 2 that is provided at an end thereof. A reference numeral 3 is a rotation center of the sample hold 2. A reference numeral 4 is a sample placed and held on the sample hold 2. A reference numeral 5 is an observing or machining point of the sample 4. Here, a coordinate system that is fixed to the charged particle beam equipment is expressed by the X-axis and Y-axis, whereas an optical axis of the optical system represented by an alternate long and short dash line is a Z-axis Moreover, a coordinate system that is fixed on this sample holder 10 and moves horizontally together with the holder is represented by the x-axis and y-axis. The movement in an XY plane of the sample holder 10 shall be performed independently from the rotary mechanism. Moreover, the XY plane (plane of Z=0) fixed to the charged particle beam equipment shall be located at the same height as an xy plane (plane of z=0) of the coordinate system that moves with the sample holder. In other words, it may be understood that a center of an image observation and recording device, such as a phosphate plate or monitor, is immobile to the origin of the XY plane and that the sample position can be moved together relatively with the xy coordinates.

As schematically shown in FIG. 1A, the sample holder 10 is provided with driving devices 7, 8 for making the holder plate 1 move in an X-axis direction and in a Y-axis direction, respectively, and the rotatable sample holder 2 is provided with a driving device 9 for making this rotate. Each driving device is driven by the computer in response to a signal given by the operator. Moreover, position sensitive detectors 7', 8' are added between the holder plate 1 and the charged particle beam equipment, and detect a position of the holder plate 1. If needed, a rotation angle detector 91 is added to the driving device 9, and detects the rotation angle of the sample hold 2. That is, the position sensitive detectors 7', 8' detects a position in the XY plane when the sample holder 10 is installed in the charged particle beam equipment or when the driving devices 7, 8 make it move. The rotation angle of the sample hold 2 is detected by the rotation angle detector 9' added to the driving device 9. In this occasion, since the position in the sample that is put under observation or to machining is always within an area including the origin of the XY plane in its center, it is convenient to describe anew the position in the sample to be put under observation or to machining by a position (x, y) of the coordinate system fixed to the holder.

In FIG. 1A, it is presupposed that the observing or machining point 5 of the sample 4 exists at a point $(x_1, y_1)$ of the xy coordinate system fixed to the holder, and the rotation center 3 of the sample hold 2 exists at a point $(x_0, y_0)$ of the xy coordinate system. This is because it is presupposed that the origin (0, 0) of the xy coordinate system does not agree with the rotation central axis, for further generalization.

FIG. 1B is a diagram showing a result of having given rotation of a rotation angle $\theta$ to the sample hold 2 by the driving device 9. The position $(x_1, y_1)$ of the observing or machining point 5 rotates around the rotation center 3 $(x_0, y_0)$ of the rotary mechanism of the sample etc. as a center, and travels to a point $(x_2, y_2)$ in the xy coordinate system.

FIG. 1C is a diagram showing a result of a movement of a vector quantity $\Delta=(x_1-x_2, y_1-y_2)$ in order to cancel out the travel incident to the rotation of a rotation angle $\theta$ with correction by a movement in the X-axis direction and in the Y-axis direction. Components $(\Delta x, \Delta y)$ to respective directions are expressed by Formula 1 and Formula 2.

[Formula 1]
$$\Delta x = x_1 - x_2 = (x_1 - x_0)(1 - \cos\theta) + (y_1 - y_0)\sin\theta \quad (1)$$

[Formula 2]
$$\Delta y = y_1 - y_2 = (y_1 - y_0)(1 - \cos\theta) + (x_1 - x_0)\sin\theta \quad (2)$$

Furthermore, the formulas are generalized to a case where the XY plane in the XY coordinate system makes an angle with the xy plane of the rotary mechanism. FIG. 2A is the same diagram as FIG. 1A. FIG. 2B is a diagram of consideration of a case where the xy plane is inclined by an angle $\psi$ around the y-axis as a center from this state, assuming inclination of the side holder plate 1 of the side-entry type sample holder 10. What is shown by a broken line in the figure is a state of an inclination $\psi=0$. FIG. 2C is a diagram showing a result of having rotated the holder plate 10 inclined as shown in FIG. 2B, and is the diagram corresponding to FIG. 1C. In this case, although the amount of movement $\Delta_{yg}$ in the Y-axis direction for correction of the displacement incident to the rotation does not differ from what is described above, the amount of movement $\Delta_{xg}$ in the X-axis direction needs to be modified by the inclination $\psi$. This is expressed by Formula 3 and Formula 4.

[Formula 3]
$$\Delta x_g = (x_1 - x_2)\cos\varphi = \{(x_1 - x_0)(1 - \cos\theta) + (y_1 - y_0)\sin\theta\}\cos\varphi \quad (3)$$

[Formula 4]
$$\Delta Y_g = y_1 - y_2 = (y_1 - y_0)(1 - \cos\theta) + (x_1 - x_0)\sin\theta \quad (4)$$

Here, the position on the optical axis, i.e., the position (height) in the Z-axis direction of the observing or machining position $(x_1, y_1)$ also varies. This shall be corrected by the optical system by adjusting a focus (focal point). Moreover, it should be noted that an angle that the charged particle beam forms with the observing or machining position $(x_1, y_1)$ is different between before and after the rotation. That is, when the inclination ψ=0, the charged particle beam is always incident perpendicularly on the plane of the sample 4, whereas when the inclination ψ≠0, the charged particle beam is incident on the plane of the sample at mutually different angles before and after the rotation, respectively. This difference in angle is fundamental, and so in order to compensate this, it is necessary to give deflection to the charged particle beam upstream of entering of the charged particle beam into the sample 4.

Enumerating procedural steps of correction for rotation by the present invention, they will be as follows.

(1) Detection of the rotation center coordinates $(x_0, y_0)$ of the rotary mechanism: As described above, there is no guarantee that the coordinates $(x_0, y_0)$ of the rotation center 3 of the rotary mechanism agree with the optical axis of the optical system of the charged particle beam. Therefore, the sample is placed and held on the sample hold 2 of the sample holder 10, and subsequently the coordinates $(x_0, y_0)$ of the rotation center 3 of the rotary mechanisms is found by performing an appropriate rotation operation on the sample hold 2. For example, two points A, B are set arbitrarily in the image of the sample when the sample 4 is set, and the same points in the image of the sample after being rotated by θ are represented by A', B'. If a position at which the line segment AA' and the perpendicular bisector of the line segment BB' crosses is found, this point will be coordinates $(x_0, y_0)$ of the rotation center 3. Therefore, the operator makes the arbitrary two points A, B in the image of the sample when the sample 4 is set be displayed on the screen by moving a cursor or by other way, and makes the computer read the coordinates of this point. Next, after only the sample hold 2 is rotated by θ, the position points A', B' that are arbitrary two points A, B in the image of the sample previously specified after the rotation are displayed on the screen, and the computer is made to read these coordinates. The computer can calculate the coordinates $(x_0, y_0)$ of the rotation center 3 from the coordinate data of four points thus obtained. The displayed points and auxiliary lines of the line segment AA' etc. may be shown on the screen if necessary and may be erased when they become unnecessary.

(2) Detection of an observing or machining point $(x_1, y_1)$ that agrees with the optical axis (penetration point of charged particle beam): When according to a study or working purpose, the sample image displayed on the monitor is a location that is intended to be observed or machined, position signals given by the position sensitive detectors 7', 8' become an observing or machining point $(x_1, y_1)$.

(3) Entry of rotation angle θ, or detection of rotation angle θ after actual rotation: A rotation angle θ of the sample hold 2 that is intended is given to the driving device 9. Alternatively, what is necessary is just to detect the rotation angle θ after the action using a signal of the rotation angle detector 9'.

By the procedure up to this, each value of $(x_0, y_0)$, $(x_1, y_1)$, and θ becomes already known. However, when using the rotation angle detector 9', θ is detected after the action. Following this, position correction incident to the rotation is completed by a procedure below.

(4) The amount of correction movement by the above-mentioned Formula 1 and Formula 2 is calculated by the computer.

(5) Based on the result by the above-mentioned (4), the computer sends a signal to the driving devices 7, 8 and makes movement for the correction. As a result of this, a position $(x_2, y_2)$ after the rotation agrees with the initial position $(x_1, y_1)$ of the optical axis.

(6) The point $(x_2, y_2)$ after the rotation and the correction movement is regarded as a new position of the optical axis $(x_1, y_1)$.

When a new rotation operation is needed, what is necessary is just to repeat the procedure from the (3) to (6) sequentially each time needed. If this procedure is performed, the observation or machining position can be made to always agree with the point at which the charged particle beam penetrates (intersection point of the optical axis and the sample plane) for a rotation of any azimuth. The above operation is common in each device having a rotary mechanism. If this operation is made to affect a plurality of rotary mechanism devices that are provided in the equipment along a flow direction of the charged particle beam (Z-axis direction), it becomes possible to interlock those devices as a result.

Hereafter, an electron microscope will be explained as an example.

FIG. 3 is a schematic diagram showing a configuration of the electron microscope equipped with two-stage electron biprisms to which the present invention is applied. A reference numeral 10 is a sample holder, 20 an objective aperture holder, 30 a selected area aperture holder, 40 a first electron biprism, 50 a second electron biprism, and 60 an observation plane, which are arranged sequentially along the flow of the electron beam (Z-axis 6). In order to avoid complicatedness, the diagram is drawn by omitting components on the electron optical system, such as a plurality of magnifying lenses. A charged particle beam source 120 and a condenser optical system 130 are provided upstream of the sample holder 10, forming the light source (crossover) 100. An objective lens 71 is provided downstream of sample holder 10, a first magnifying lens 72 is provided downstream of the selected area aperture holder 30, and a second magnifying lens 73 is provided downstream of the first biprism holder 40, respectively. A reference numeral 110 is a vacuum vessel, in which the above-mentioned various holders, a charged particle beam source, an irradiation optical system, various lenses, an observation plane, etc. are provided.

The sample holder 10 was explained in FIG. 1 and FIG. 2, and each of the objective aperture holder 20, the selected area aperture holder 30, the first electron biprism holder 40, and the second electron biprism holder 50 is equipped with a holder plate and a rotation part that correspond to the reference numerals 1 and 2, like the sample holder 10. Moreover, the electron microscope is equipped with a driving device corresponding to the reference numerals 7, 8, and 9 that drives the holder plate in the X-axis direction and in the Y-axis direction in the XY coordinate and makes the rotation part rotate and is equipped with a position sensitive detector and a rotation angle detector corresponding to the reference numerals 7', 8', and 9'. Incidentally, when describing "make the holder rotate" or "rotation center of the holder" in this specification, it means "make the rotation part of the holder rotate" or "rotation center of the rotation part of the holder."

In FIG. 3, display of a driving device, a position sensitive detector, and a rotation angle detector is omitted since otherwise the diagram would be complicated. As a substitute for this, boxes 201 to 205 are displayed and each of the boxes 201 to 205 is connected with each holder by three lines. Here, a reason that the number of lines is specified to be three is to mean that three elements consisting of two driving devices for driving it in the X-axis direction and in the Y-axis direction, one driving device for making the rotation part rotate, and position sensitive detectors for them are mutually independent and they act independently. The boxes 201 to 205 representing these driving devices, the position sensitive detectors, and the rotation angle detectors perform the following functions: transmitting an operation signal given from a control computer 300 through driving system microcomputers 310$_1$ to 310$_5$ to the driving device; driving the holder; and at the same time sending signals detected by the position sensitive detector and the rotation signal detector back to the control computer 300. Reference numerals 320, 330 are input means and a display device of the control computer 300, respectively.

Incidentally, a case where the sample holder 10 is inclined by ψ as described by FIG. 2B is omitted. In the case where the equipment is configured to support this inclination, what is necessary is that the equipment shall be equipped with a driving device for controlling the inclination of the holder plate 1 and its rotation angle detector and they shall be controlled by the control computer 300 like the control by other driving device and its position sensitive detector and rotation angle detector.

It is configured that an image input device (for example, a camera) 410 shall be disposed for the observation plane 60, this output shall be displayed on an image observation monitor 420, which enables the operator to view the output, and shall be recorded by the image recording device (for example, a video apparatus) 430 as data. Furthermore, on the image observation monitor 420, the operator can specify a point at an arbitrary position and make it displayed on the display screen using input means, for example, a mouse, and the control computer 300 is equipped with a function of being able to read these coordinates.

While viewing the image observation monitor 420 with the sample being set, the operator enters the operation signal through the input means 320 of the control computer 300 so that the purpose of observation can be attained. The control computer 300 is equipped with a necessary program, calculates a manipulated variable in response to an operation signal, and sends it to a driving device. Moreover, an operation result of the driving device is detected by the position sensitive detector and the rotation angle detector and is fed back. Furthermore, data on the display screen of the image observation monitor 420 is introduced into the control computer 300 as needed, like the detection of the rotation center described above. The display device 330 of the control computer 300 displays a signal given by the operator, working conditions of the electron microscope, and a working situation of the electron microscope, which are used as information for the next operation that corresponds to a change appeared on the image observation monitor 420 incident to an operation of the operator.

FIG. 4 is a block diagram for explaining more concretely a relation between the control computer 300 and holders 10-50 that is related with the operator's operation. In addition to a common keyboard and a common mouse, the input means 320 of the control computer 300 shall be equipped with operation knobs each of which enables a rotation instruction of each holder to be given by the operator's rotation operation and each of which enables knob operation for horizontal movement. A reference numeral 340 is a microcomputer for reading that converts a result of an operation of the operation knob by the operator into a signal that the control computer 300 can use. A body of the control computer 300 has a central processing unit (CPU), program storing memory, information storing memory, and work memory that are connected by a bus, calculates the manipulated variable by performing processing in response to the signal given by the operator. The obtained manipulated variable is sent to the driving device through the driving system microcomputers 310$_1$ to 310$_5$. Here, only the sample holder 10 and the first electron biprism 40 are shown as holders. FIG. 1 and FIG. 2 explain concretely the sample holder 10. As a brief explanation of the first electron biprism 40, it substantially consists of the holder plate 1 and the rotation part 2', like the sample holder 10. The interior of the rotation part 2' is formed hollow, and an electron beam can pass through this hollow part. A filament electrode 41 of the electron biprism is installed in the center of the hollow part, and ground electrodes 42, 43 parallel to the filament element 41 are installed on both ends thereof. The filament electrode 41 and the ground electrodes 42, 43 are rotated as one body when the rotation part 2' rotates. The filament electrode 41 is given an electrical voltage from the outside, and is made to deflect the electron beam.

Basic matters regarding a display device 330 and a rotation operation by the operator will be explained. Here, display examples of the display screen 330 of the control computer 300 and of the image observation monitor 420 are shown. In the display screen 330, the holder that is an object of a rotation operation is displayed in the order of a sample holder, an objective aperture holder, the selected area aperture holder, a first electron biprism holder, and a second electron biprism holder, which is the same order of arrangement of the actual electron microscope. For each holder, it is made possible to specify the rotation angle and increase/decrease of its value (for example, left-handed rotation is represented by increase (+) and right-handed rotation is represented by decreases (−) in FIG. 1). A display corresponding to this is shown. Here, as initial setting, a state where all the holders are specified to have a rotation angle of 5° is displayed. When the operator wishes to set another value to the rotation angle, the operator can alter a value of rotation angle of the holder to be altered to a desired value through the input means 320. Regarding increase/decrease of the rotation angle, the operator can click and specify a rectangular display that is displayed and increase/decrease it according to the click. The amount of change of increase/decrease of the rotation angle corresponding to one click can be set arbitrarily and independently. A rotation operation can be done by an operation knob for allowing the operator to set it by the operator's rotation operation. In this case, for example, when the operator selects "Arbitrary" of rotation and operates the operation knob, an operation angle is read by the microcomputer 340 and is given to the control computer 300.

Moreover, which holder is interlocked for a rotation of each holder can be specified by selecting "All" or "Only below" of Link. When not making a link, or when canceling it, what is necessary is just to select neither of them. Incidentally, what is necessary for the holders specified by Link is just to interlock the holders correspondingly to the rotation of the holder that becomes an object of the operation. However, a link may be such that a link is only made from the upper to the lower but is not made from the lower to the upper. For this purpose, desirably it is configured as follows, for example: when the all are interlocked regardless of the order of arrangement, a display of link "All" is supposed to be selected, and when a link is made only for what has an arrangement order from the upper to the lower, "Only below" is supposed to be selected. If selection was done in this way, for example, when Link A is selected in "Only below;" for a rotation instruction of the sample holder 10, the selected area aperture holder 20 and the first electron biprism 40 are interlocked. However, for a rotation instruction of the selected area aperture holder 20, only the first electron biprism 40 is interlocked, and the sample holder 10 is not interlocked. If it is done in this way, it becomes possible not only to determine an effect of each element on the rotation individually but also to actually deal with a plurality of links by a single link display. Therefore, saving of space of a display monitor can be attained, and complicatedness of display can be avoided.

Here, for links, an example where A, B, C, and D can be selected is shown. Link A clearly shows by an indication of a circle symbol that the sample holder, the selected area aperture holder, and the first electron biprism holder are interlocked. Similarly, indication of a round symbol clearly shows that in Link B, the sample holder, the first electron biprism holder, and the second electron biprism holder are interlocked, and that in Link C, the sample holder, the first electron biprism holder, and the second electron biprism holder are interlocked, respectively. In making the links, interlocking operations that are likely to be done frequently, for example, it is advisable that they are determined as shown Links A to C. However, in the case where displaying all the settings makes the screen hard to see, what is necessary is just to limit to only representative settings and to make other interlocking settable by the operator. For this purpose, what is necessary is, for example, just to select Link D and configure the equipment to allow the operator to select holders to be interlocked like specification of increase/decrease of the angle. In the case where each rotary mechanism is intended to be operated individually, what is necessary is just not to make links. When the operator enters the selection of links from the input means 320, it is desirable that the equipment is configured to be able to clearly demonstrate which links are selected among Links A, B, C, and D by changing a color of background of characters of the selected links or by other way.

The rotation center coordinate $(x_0, y_0)$ of the rotary mechanism is detected prior to the rotation operation. For this purpose, what is necessary is just to perform detection using an image observation monitor 420 image, as described above.

The display device 330 and the method of each operation described above are just one example and the both are not limited to what is described here. Hereafter, regarding a link related to the rotation of the holder, a relation between the operator's operation and the computer's action will be explained. Here, the following is presupposed: a sample is placed and held on the sample holder 10; the sample holder 10, the objective aperture holder 20, selected area aperture holder 30, the first electron biprism 40, and the second electron biprism 50 are inserted into the body of the electron microscope; the charged particle beam source 120, the condenser optical system 130, the objective lens 71, the first magnifying lens 72, and the second magnifying lens 73 are set to respective initial states; and the electron microscope starts from a normally operating state.

(Determination of Rotation Center)

FIG. 5 is a diagram showing a flow for determination of the rotation center of the sample holder. In FIG. 5, Steps 501, 503, and 505 are processing of executing the above-mentioned procedure from steps (1) to (3). Although it is the procedure to find the rotation center of the sample holder, it is necessary to find the rotation center positions $(x_0, y_0)$ for the all holders. Therefore, in the case where links are made and interlocked, processing of finding the rotation center is executed for all the holders collectively in advance. In this case, for each holder, like the sample image, attention-focused two points are displayed in an image of the each holder appearing on the monitoring screen 420 on the screen, are entered into the computer, and are subjected to a rotation operation. The attention-focused two points after the rotation are displayed in the image on the screen, and are entered into the computer. This process will be repeated. Incidentally, interlocking needs to be canceled in this stage.

(Link 1: In the Case of Rotating the Sample)

When image formation is performed aiming at a predetermined electron diffracted wave, usually it is enough to rotate only the objective aperture. In the case, for example, where the detector to be placed in the observation plane 60 (such as film) has direction dependency, a sample shape must be adjusted to it, and accordingly there arises a possibility that both the sample and the aperture will need to be interlocked.

[I] In the Case of a Single Crystal Sample

It is presupposed that the sample, the objective aperture, and the selected area aperture are already inserted on the optical axis and that, as described above, the rotation center $(x_0, y_0)$ of the sample holder 10, the rotation center $(x_0, y_0)$ of the objective aperture holder 20, and the rotation center $(x_0, y_0)$ of the selected area aperture holder 30 are obtained. Here, an expression of the rotation center $(x_0, y_0)$ was explained by FIGS. 1 and 2 only for the sample holder 10, since the same coordinate expression can be applied to other holders, the same expression will be used for them. Such appropriation is applied to other coordinates similarly. Hereafter, explanation will be given with reference to FIG. 6. It is presupposed that other constituents having no bearing on the interlocking, for example, the electron biprism etc., are disposed in appropriate positions that do not hinder the following works.

(1) The operator makes the sample holder 10 move in the XY plane while viewing an image on the image monitor 420, determines a location where the operator wishes to observe, namely, a position $(x_1, y_t)$ of the sample that is put to observation, and enter the position $(x_1, y_1)$ of the sample into the computer by, for example, pressing the enter key (Step 601).

(2) The operator determines a magnification with which observation and recording are performed and enters it into the control computer 300 through the input means 320 (Step 603). By these steps, working conditions of lenses (a magnification, a focal length, etc.) of the optical system are fixed.

(3) A wavelength of the electron beam to be used and a focal length of the objective lens determine the move distances, such as for correction of displacement, incident to the rotation of the objective aperture holder 20 (Step 605).

(4) Since the magnification of the objective lens is fixed in Step 603, a ratio of the move distance of the selected area aperture holder to the horizontal move distance of the sample holder will be fixed (Step 607). Incidentally, the same result as in Step 607 can be obtained, not from the magnification of the lens but mechanically. That is, from the amount of mechanical movement of the sample holder 10 that is required when the operator makes a certain one point in the sample image move by a fixed distance while viewing the image monitor 320 and the amount of mechanical movement of the selected area aperture holder 30 that is required when the operator makes an arbitrary one point fixed on an image of the selected area aperture move by the same distance, the control computer 300 finds a relative magnification of coordinate systems. However, it is assumed in this case that the fine movement of each holder is equivalent.

(5) While viewing the image monitor 320, the operator checks a sample shape, selects a selected area aperture of a proper shape (direction) (Step 608), and makes the selected area aperture rotate and move horizontally to match the selected area aperture to the sample shape (Step 609). By this procedure, the horizontal position ($x_1$, $y_1$) of the selected area aperture is fixed.

(6) The operator switches over to diffraction pattern observation (Step 614), and performs the followings while viewing the image monitor 420: checking a direction by the electron diffraction pattern; selecting an objective aperture of a proper shape (direction) (Step 610); making the objective aperture rotate in conformity to the electron diffraction pattern orientation and move horizontally; and matching the objective aperture to the electron diffraction pattern (Step 611). By this procedure, the horizontal position ($x_1$, $y_1$) of the objective aperture is fixed.

By the procedure from (1) to (6), relative relations among the sample, the objective aperture, and the selected area aperture are finalized.

(7) The operator can return to an observation state of the sample image (Step 612), set up Link C shown in FIG. 4 (Step 613), and while viewing the monitoring screen 420, make them rotate and move horizontally while they are interlocked so that they may take an orientation most effective for an observation purpose. That is, if a rotation angle required for sample image observation is entered (Step 615), all the works will be automatically ended.

Incidentally, although the selection of the selected area aperture and the objective aperture was not explained in FIG. 3, normally a plurality of these elements are installed in the electron microscope, and some of them are selected and used according to the shape of the sample etc. In the above explanation, the selection of the selected area aperture and objective aperture performed in Steps 608 and 610 is one of works that are frequently done usually.

[II] When Changing Observation Location in the Case of a Single Crystal Sample

While viewing the monitoring screen 420, the operator makes the sample holder 10 move in the XY plane in search of a new observation location, and fixes a position of the sample ($x_1$, $y_1$) to be put under new observation (Step 601). Unless an observation magnification is changed very largely, it is not necessary to change the magnification of the objective lens (Step 607 is unnecessary). Matching to the shape of the sample, the size and/or shape of selected area aperture are altered (Step 608), and matching thereof by rotation and movement (Step 609) is resumed. Since in the case of a single crystal sample, crystal orientation of the sample does not depend on the observation location; even when the observation location is changed, alteration of the objective aperture (operation of procedure (6) in the above-mentioned case of [I] a single crystal sample (Steps 610 and 611)) is unnecessary. By performing Steps 613 and 615 after this, the work is completed.

When observation is performed by changing largely the magnification of the objective lens 71, the whole processing of Step 603 and after is performed.

[III] When an Observation Location is Changed in the Case of a Polycrystalline Sample A procedure when the polycrystalline sample is observed instead of the above-mentioned single crystal sample is the same as that was explained with reference to FIG. 6. Here, a case where the observation location is changed after the polycrystalline sample under observation was observed by the above-mentioned procedure will be described.

Since in the polycrystalline sample, the crystal orientation changes depending on sample positions, the shape and size of the objective aperture become objects of reexamination. Therefore, what is necessary is that while viewing the monitoring screen 420 of the sample, the operator makes the sample holder 10 move in the XY plane in search of a new observation location, and fixes a position of observation ($x_1$, $y_1$) to be put under new observation (Step 601), and executes processing of Step 608 and after. Unless the observation magnification is changed very largely, it is not necessary to change the magnification of the objective lens (Step 607 is unnecessary), which is the same as [II] change of the observation location of the single crystal sample.

When observation is performed by largely changing the magnification of the objective lens 71, the whole processing of Step 603 and after is performed, which is the same as position alteration of the single crystal sample.

(Link 2: In the Case of an Interference Optical System)

Regarding the case of a triple-biprism electron interferometer, explanation will be given with reference to FIG. 7. It is presupposed that the observation is started from a state where the sample is inserted in advance, the monitoring screen 420 is displaying a sample image nearly at an observation position as an observation screen of the electron microscope, and the magnification is finalized. Moreover, it is presupposed that the rotation correction of the electron biprisms is in a state where it can be executed if the rotation center is obtained. Incidentally, objective aperture etc. not explained is disposed at a position that does not hinder the following works, which is the same as the above-mentioned Link 1.

[I] In the Case where the Three Electron Biprisms can be Regarded Equivalent Mechanically It is presupposed that the three electron biprisms are in the same state (triplicate), and a deflection characteristic to the electron beam, the thickness of the filament electrode, initial setting of the fine adjustment are all the same.

First, the upper-stage electron biprism is inserted in the image plane of the sample, Steps 501, 503, and 505 explained in FIG. 5 are executed, and the rotation center ($x_0$, $y_0$) is found (Step 701). In this occasion, the arbitrary two points on the image that the operator gives are dirt adhered on the filament electrode or the like as a clue. Next, the intermediate-stage electron biprism is inserted in the image plane of the sample, and the rotation center ($x_0$, $y_0$) is found similarly (Step 703). Moreover, the lower-stage electron biprism is inserted, for example, between the image plane of sample and the image plane of the light source, and the rotation center ($x_0$, $y_0$) is found similarly (Step 705). Although focusing is not performed on the filament electrode of the lower-stage electron biprism, the same work as those of the upper and lower-stage electron biprisms that are in focus can be performed by viewing a shadow.

Next, since the diameter of the filament is assumed to be the same, the size (diameter) of an image of a shadow of the filament appeared on the monitoring screen 420 is found and entered into the computer (Step 707). By this procedure, the relative magnification of the each is fixed and the computer can calculate the relative ratio of the horizontal move distances of three stages of (the upper, intermediate, and lower) electron biprisms (Step 709).

Next, while viewing a monitoring screen 420, the operator finds a location of the filament electrode of the upper-stage electron biprism that is intended to be under observation, enters it into the computer (Step 711), and determines a location ($x_1$, $y_1$) of the filament electrode of the upper-stage electron biprism that is to be under observation.

Next, the operator fixes an angle of the filament electrode of the intermediate-stage electron biprism to the filament of the upper-stage electron biprism on the monitoring screen 420, and enters it into the computer (Step 713). It is best to set the angle to 90° as explained in the preceding JP No. 2004-046633, but the angle is not limited to this. After that, while viewing the monitoring screen 420, the operator finds a location of the filament electrode of the intermediate-stage electron biprism that is intended to be under observation (Step 715), and fixes a location of the filament electrode $(x_1, y_1)$ to be put under observation.

Next, while viewing the monitoring screen 420, the operator fixes an angle of the filament electrode of the lower-stage electron biprism to the filament of the upper electrode or to the filament of the middle electrode biprism (Step 717). (Since the angle of the filament electrode of the lower-stage electron biprism defines the aspect ratio of the magnitude of an interference area as was explained in the preceding JP No. 2004-046633, the angle may be altered depending on the sample size. However, it is fixed temporarily here.) After that, while viewing the monitoring screen 420, the operator finds a place to be intended to be put under observation (Step 719) and fixes a location of the lower filament electrode $(x_1, y_1)$ to be put under observation.

By the above-mentioned Steps 701 to 719, the relative relation of the three electron biprisms is finalized. Therefore, the operator is enabled to set the links shown in FIG. 4 among the three electron biprisms (Step 721), and while viewing the monitoring screen 420, makes the three electron biprisms rotate and move horizontally while they are interlocked so that they may take an orientation most effective for the observation purpose. That is, while viewing the monitoring screen 420 of the sample, the operator enters a necessary rotation angle (Step 723) for the filament of the upper-stage electron biprism, whereby all the works are automatically ended.

FIG. 8 is a flow diagram for explaining a situation where the computer executes interlocking processing in response to entry of the rotation angle by the operator (Step 723) after link setting is instructed in Step 721. First, it is determined, regarding the specification of the link, whether "All" of display is selected (Step 801), wherein "All" instructs that all the holders specified by the link shall be interlocked according to the rotation of the holder that becomes an object of the operation. If "All" is selected, the equipment makes all the holders specified by the link rotate according to the rotation angle that the operator operated or instructed based on data obtained through the procedure of FIGS. 6 and 7, and the position is corrected. If "Only below" is selected, the equipment makes the holders that are below the holder and are specified by the link rotate according to the rotation angle of the holder that the operator operated or instructed, so that the position is corrected.

Although the above explanation was made under a premise that the thicknesses of the filament electrodes of the electron biprisms are equal; an execution procedure for the case where the thickness of the filament electrode of the electron biprism is not equal, or the case where its value is unknown will be explained.

[II] If the Thickness of Filament Electrode is Already Known

If the thickness of the filament electrode is already known, the operator enters it into the computer in a stage preceding to Step 707. The computer calculates a relative ratio of horizontal move distances of three stages of (the upper, middle, and lower) electron biprisms from the sizes (diameters) of images of shadows of the filaments, although the thickness of each filament is different, in the processing of Step 709. The processing of Step 711 and after is just as in FIG. 7.

[III] When the Thickness of Filament Electrode is Unknown and Each Thickness is Different When the thickness of the filament electrode is unknown and each thickness is different, it is assumed that all the initial settings of the fine adjustments of the electron biprism holders to be used are the same, and in a stage preceding to Step 707, while viewing the monitoring screen 420, the operator makes the each electron biprism holder move, and enters the amount of mechanical movement (manipulated variable) of the electron biprism holder taken to make the electron biprism holder move across a fixed distance in the field into the computer. The computer calculates the relative ratio of the horizontal move distances of three stages of (the upper, middle, and lower) electron biprisms from this amount of mechanical movement (manipulated variable) by processing of Step 709. This is basically the same method as that of the processing performed for the selected area aperture (procedure (4) in the case of [I] a single crystal sample). Processings in Step 711 and after are as in FIG. 7.

In addition to what is described above, if the computer is informed of the magnification of a position at which each filament electrode is inserted from the electron optical system in the processing of Step 709 as a setting value, the relative ratio can be obtained based on that value.

Incidentally, when the flow reaches Step 723 and the operator wishes to alter an aspect ratio of the interference area because of a sample shape based on observation after establishment of a link among electron biprisms, what is necessary is that the operator releases each link between electron biprisms in Step 721 and restarts from setting of an angle of the filament electrode of the lower-stage electron biprism in Step 717.

Moreover, although not illustrated in FIG. 3, in the actual electron microscope, many electron lenses are arranged in its optical system. In the case where the flow reached Step 723 and, due to observation after establishment of the link among the electron biprisms, the magnification is altered by these lenses or in the case where the magnification is altered by an electron lens that exists on the observation plane 60 side closer than the lower-stage electron biprism by two or more lenses, since the relative relation of the electron biprisms can be regarded as being almost unchanged, the operator is allowed to continue observation as before. However, in the case where the magnification is altered by a lens between the electron biprisms or directly below or directly above the electron biprism, a relative magnification between the electrodes may vary. Therefore, after the operator released the link between the electron biprisms in Step 721, the operator must reestablish the link by going through all the processings in Step 707 and after.

(Link 3: Sample Rotation and the Interference Optical System)

When performing observation with the triple-biprism electron interferometer, while performing a rotation operation on the sample, the both Link 1 and Link 2 described above-must be set and the both must be used. Alternatively, the both must be put together as one link and must be dealt with so. That is, the operator fixes an observation place by executing processings shown in FIG. 6 and FIG. 7, determines conditions of an interferometer, and subsequently enters settings of the links in Step 613 and Step 721 into the computer as one link.

INDUSTRIAL APPLICABILITY

As described above, according to the present invention, when the charged particle beam adjusting devices, such as the sample holder, the variable aperture, and the electron biprism, are made to rotate in the plane perpendicular to the optical axis of the optical system of the charged particle beam or in a slightly inclining plane, a displacement of the irradiation position of the charged particle beam occurring fundamentally is corrected by canceling it out with the use of the position sensitive detector and the driving device of the equipment in concern, and the charged particle beam can penetrate through the same place even when whatever rotation in the plane in concern is performed. Moreover, by interlocking the rotary mechanisms of these plurality of devices, it becomes possible to control the plurality of rotary mechanisms more simply and with high precision, and therefore advantages that the charged particle beam equipment made up of these plurality of rotary mechanisms has can be enjoyed.

EXPLANATION OF REFERENCE NUMERALS

Figure 1A:
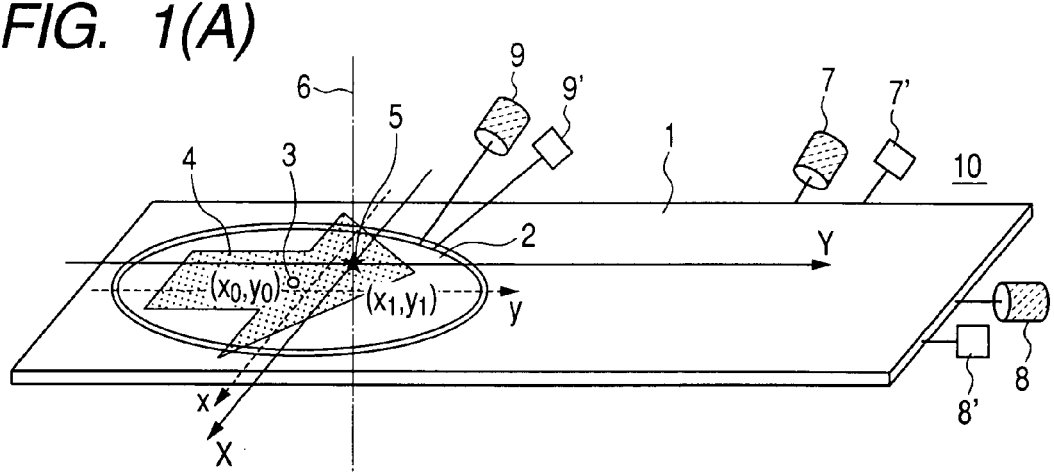
FIGS. 1A to 1C are diagrams explaining a rotation operation of a sample holder and a correction operation that becomes necessary incident to this.
Figure 1B:
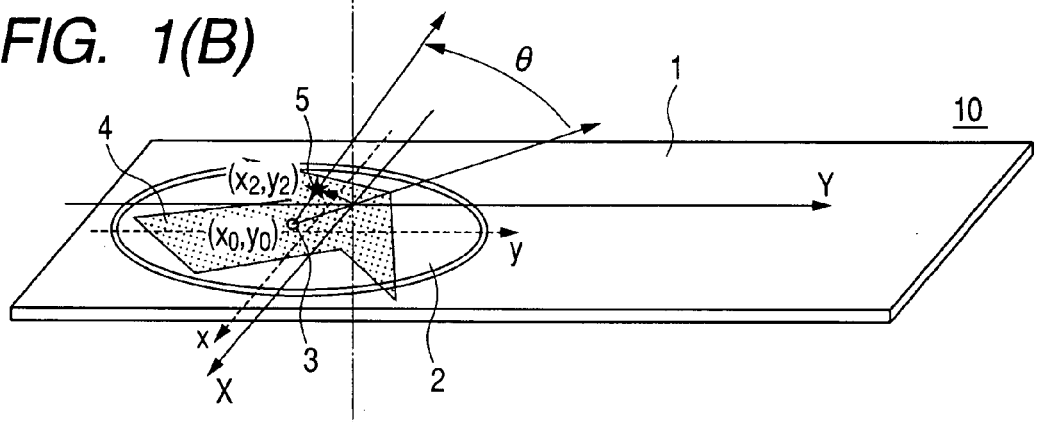
Figure 1C:
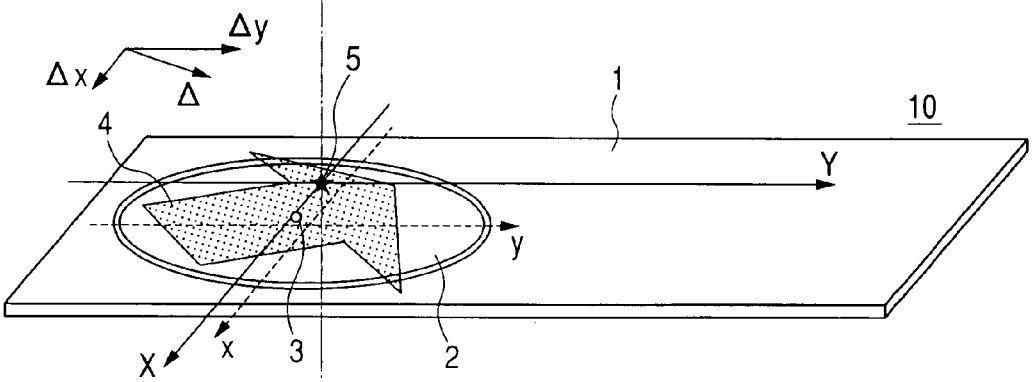
Figure 2A:
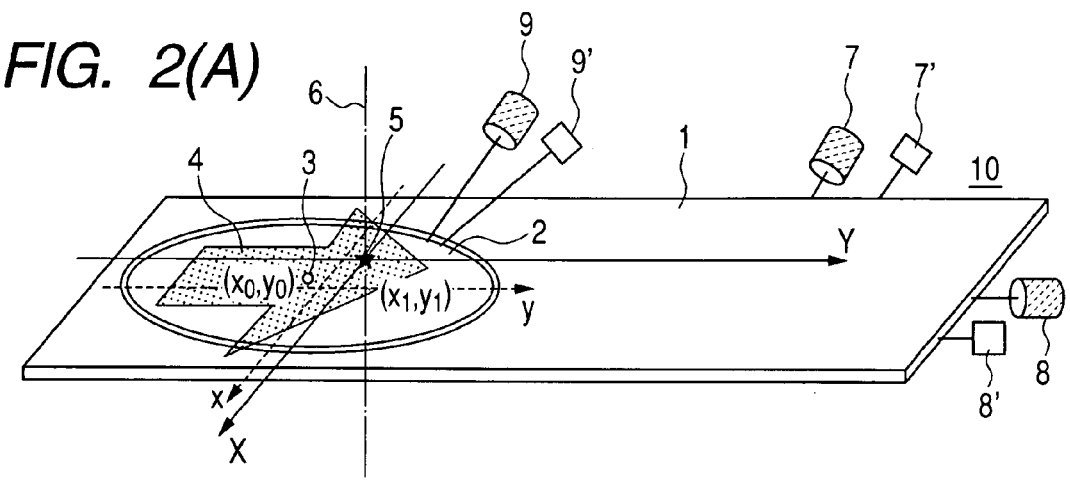
FIG. 2A is the same diagram as FIG. 1A.
Figure 2B:
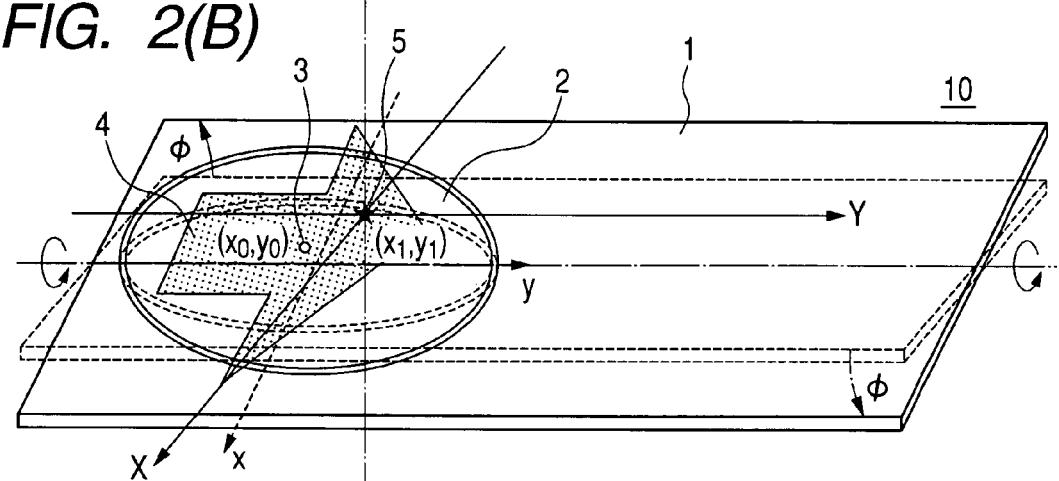
FIG. 2B is a diagram when considering a case where an XY plane of the holder plate 10 is inclined by an angle ψ around the Y axis as a center.
Figure 2C:
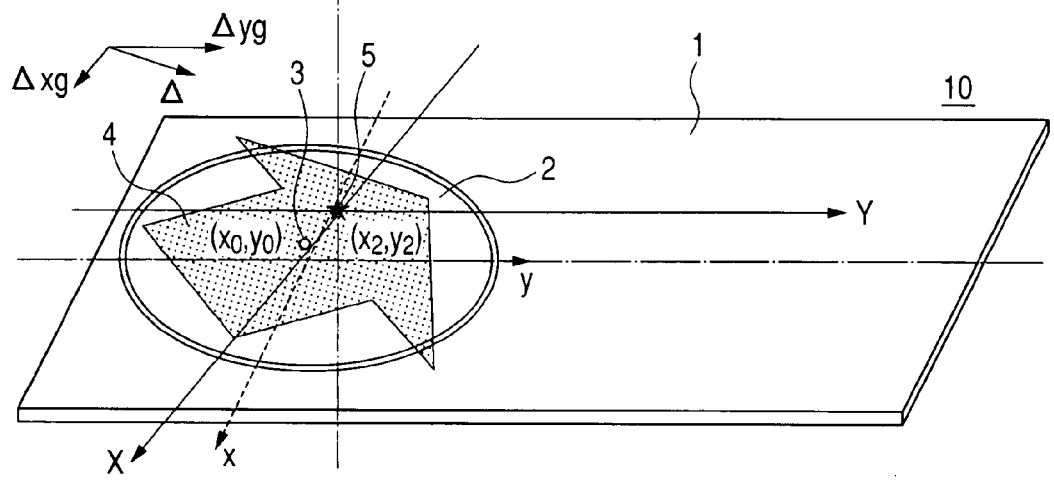
FIG. 2C is a diagram showing a result of making the inclined holder plate 10 rotate and corresponding to FIG. 1C.
Figure 3:
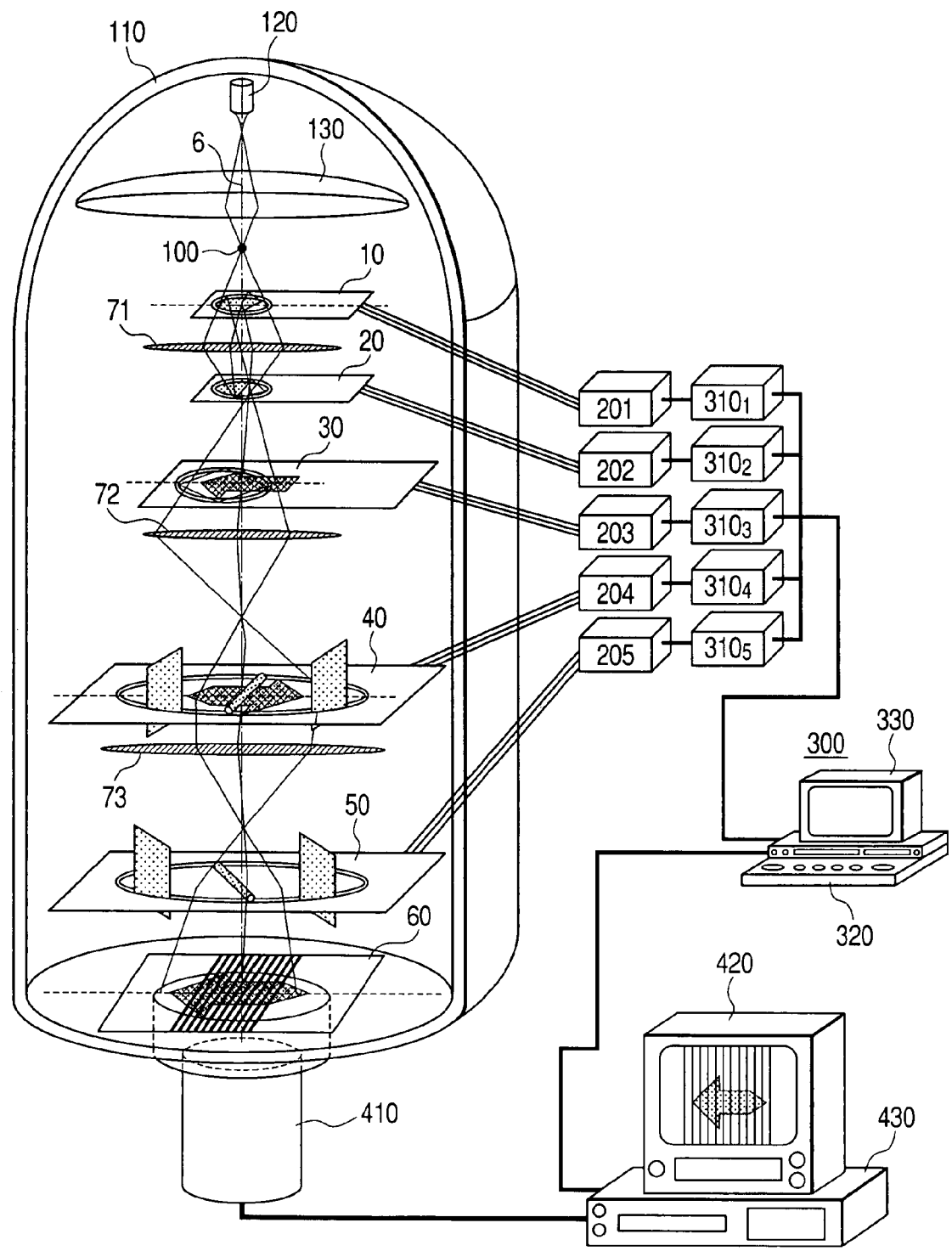
FIG. 3 is a schematic diagram showing a configuration of an electron microscope equipped with two-stage electron biprisms to which the present invention is applied.
Figure 4:
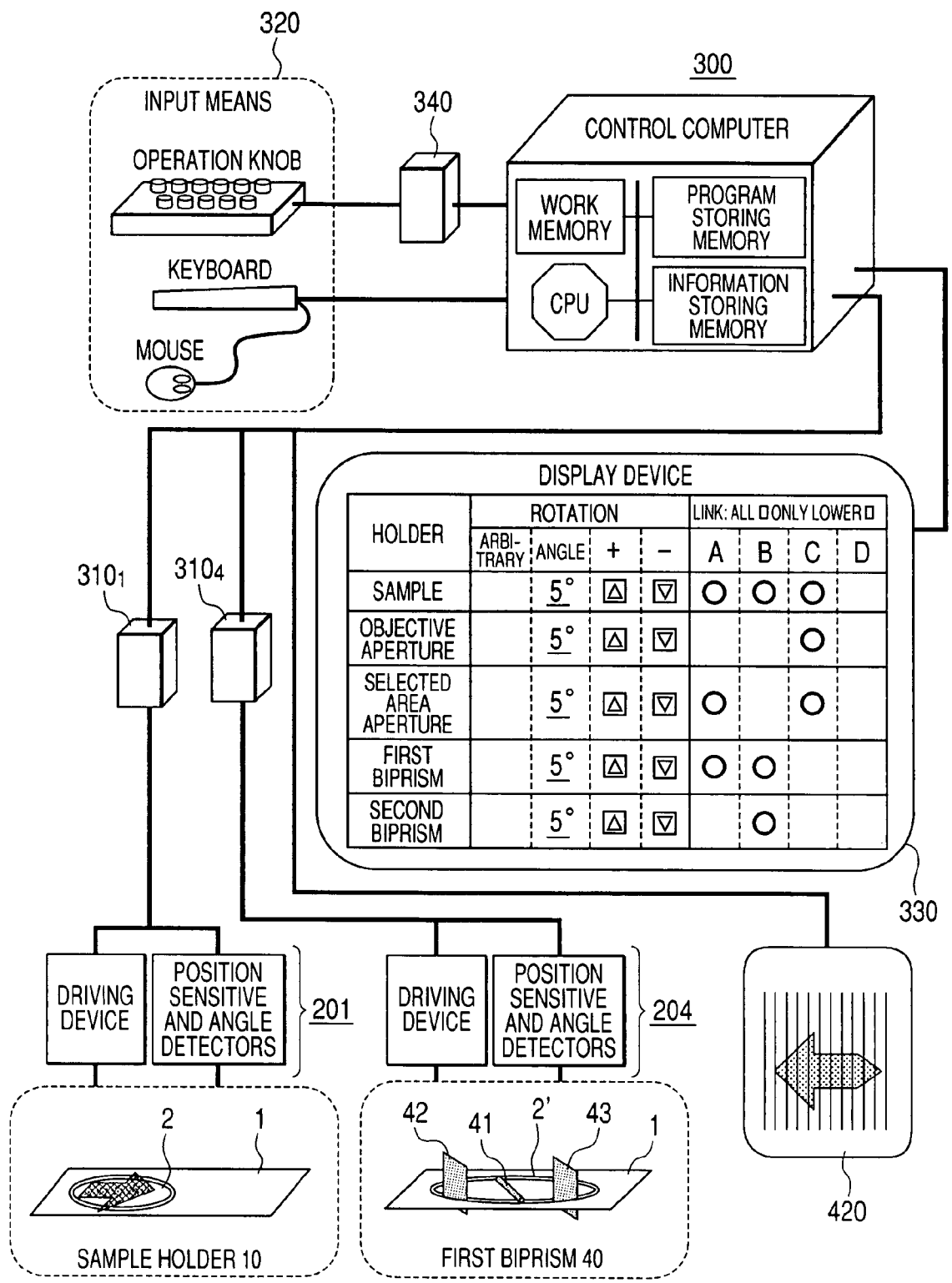
FIG. 4 is a block diagram for explaining more concretely a relation between a control computer 300 and holders 10 to 50 that is related to an operation of the operator.
Figure 5:
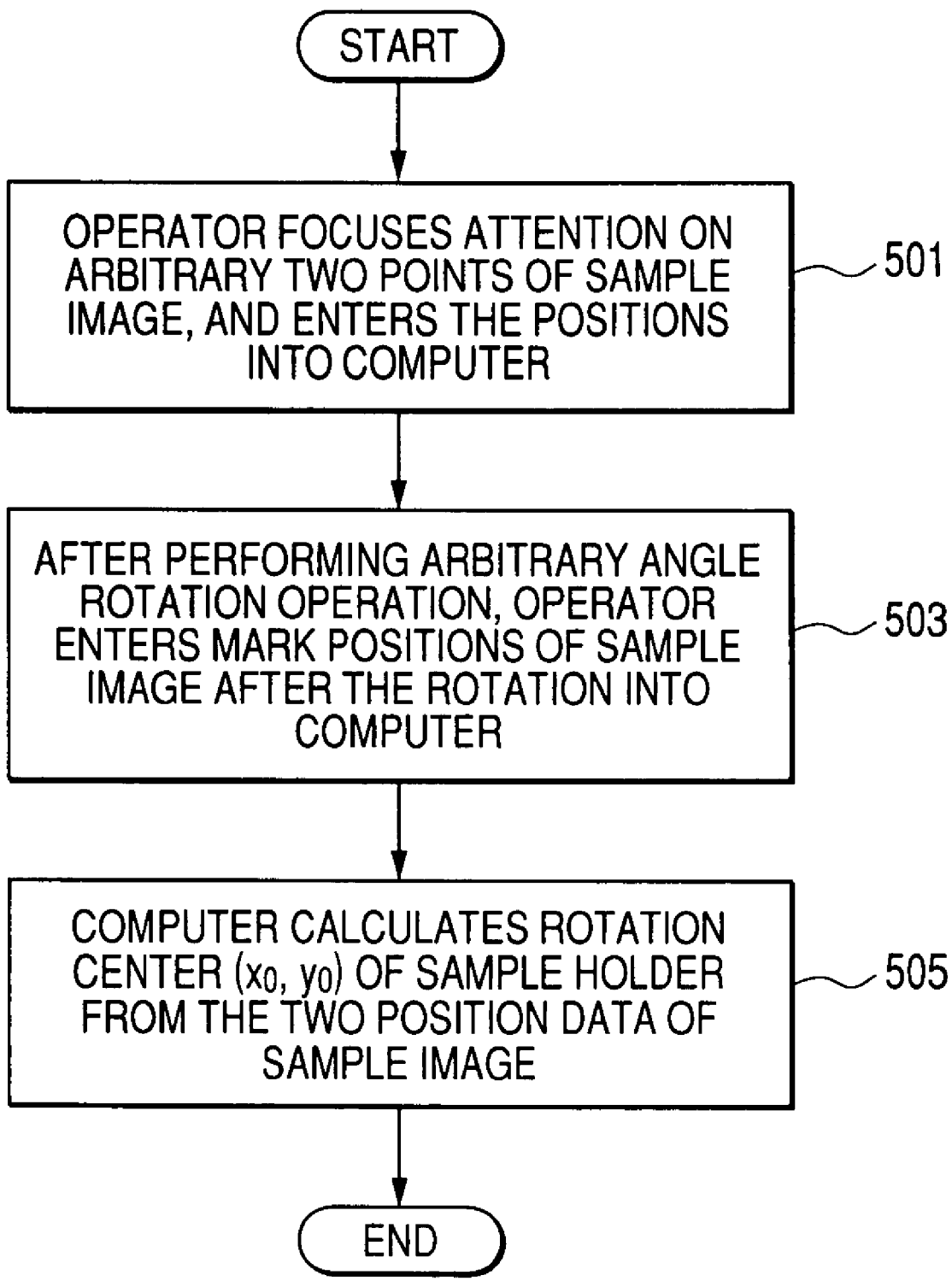
FIG. 5 is a diagram showing a flow for determination of a rotation center of a sample holder.
Figure 6:
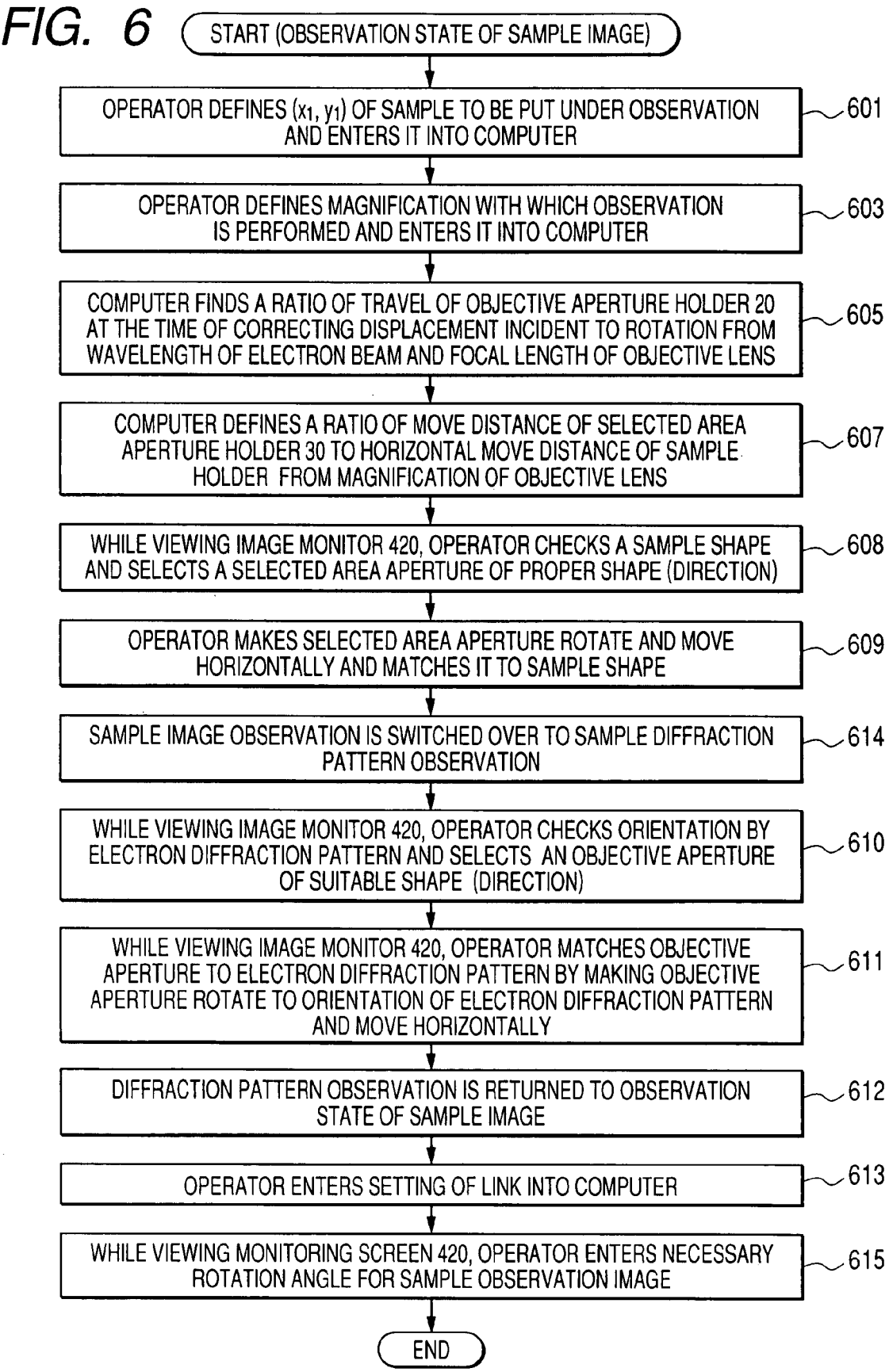
FIG. 6 is a diagram showing a flow of processing of interlocking a sample holder and an aperture holder in the case of a single crystal sample.
Figure 7:
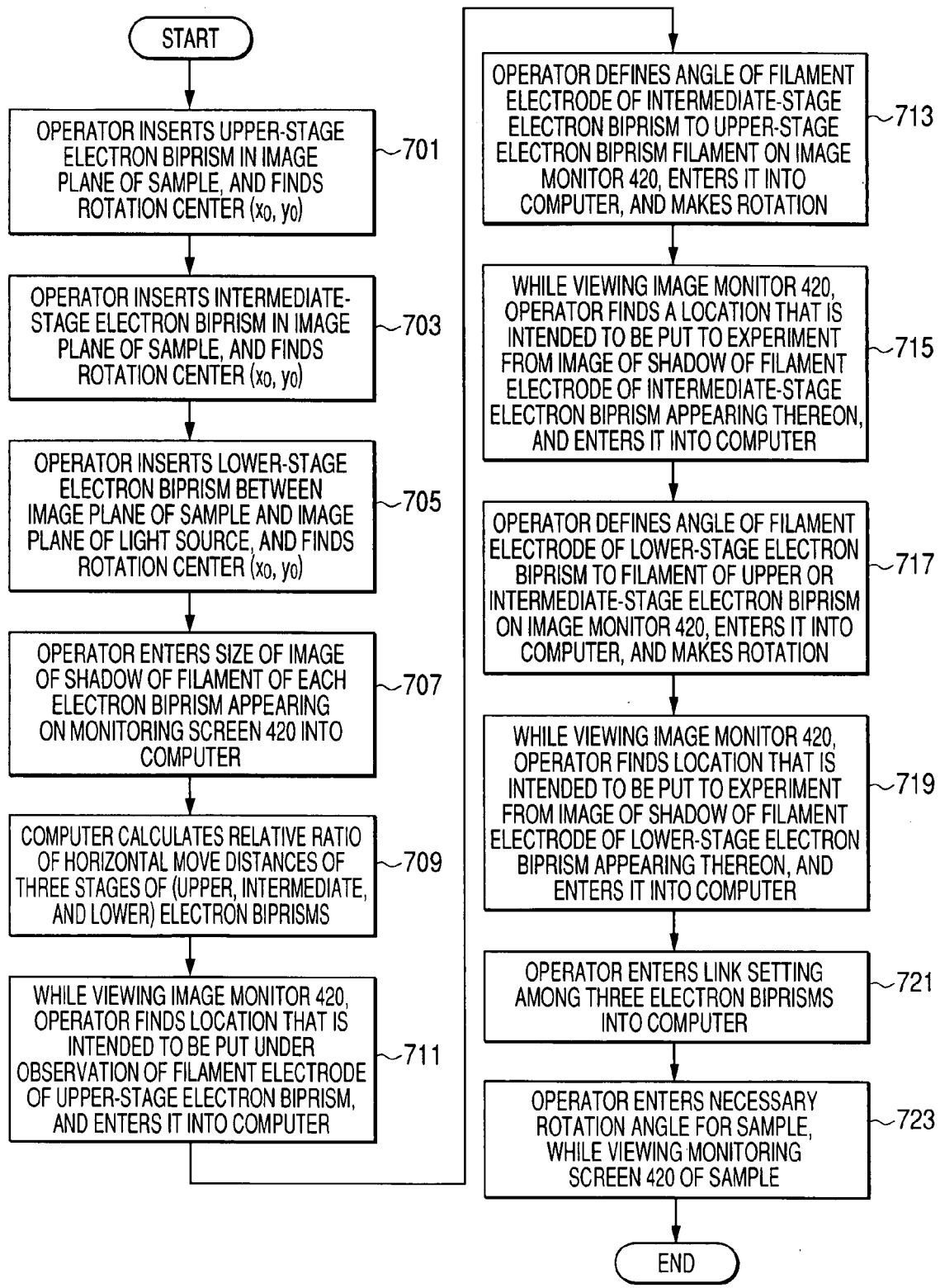
FIG. 7 is a diagram showing a flow of processing of interlocking biprisms of a triple-biprism electron interferometer in the case where the three biprisms are equivalent.
Figure 8:
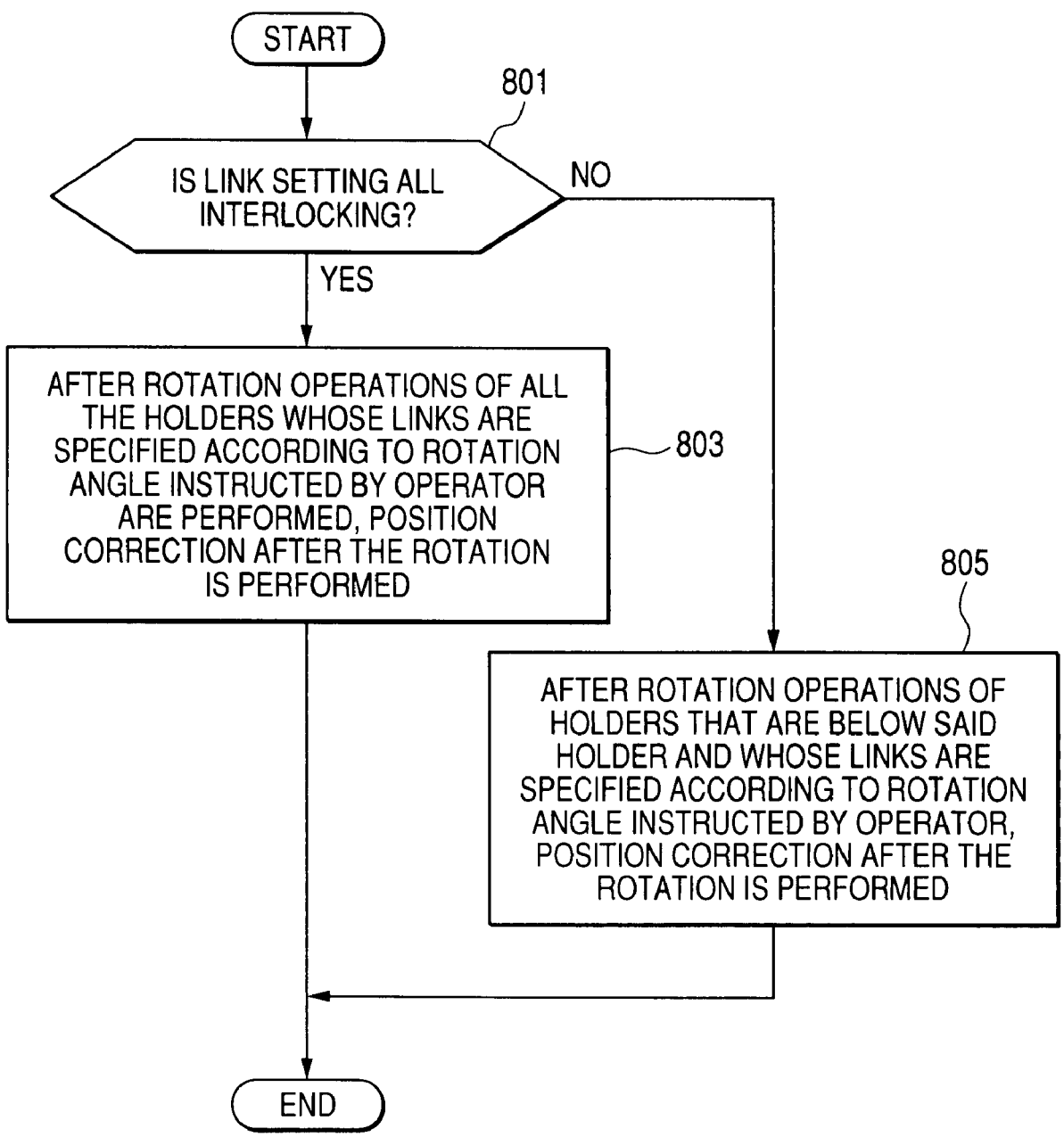
FIG. 8 is a flow diagram for explaining a situation where interlocking processing is executed by the computer in response to an entry of a rotation angle by the operator after link setting is instructed.

1 . . . Holder plate
2 . . . Sample hold
3 . . . Rotation center of sample hold
4 . . . Sample
5 . . . Observing or machining point of sample
6 . . . Optical axis of optical system
7, 8, 9 . . . Driving device
7', 8' . . . . Position sensitive detector
9' . . . . Rotation angle detector
10 . . . Sample holder
20 . . . Objective aperture holder
30 . . . Selected area aperture holder
40 . . . First electron biprism holder
50 . . . Second electron biprism holder
60 . . . Observation plane
71 . . . Objective lens
72 . . . First magnifying lens
73 . . . Second magnifying lens
110 . . . Vacuum vessel
120 . . . Charged particle beam source
130 . . . Condenser optical system
201-205 . . . Box
300 . . . Control computer
320 . . . Input means of control computer
330 . . . Display device of control computer
$310_1$-$310_5$ . . . Driving system microcomputer
410 . . . Image input device
420 . . . Image observation monitor
430 . . . Image recording device

The invention claimed is:

1. Charged particle beam equipment used for observation or machining of a sample, comprising:
   a sample holder that holds the sample rotatably in an XY plane perpendicular to an optical axis of an optical system of the charged particle beam equipment or on a slightly inclining plane and holds the sample movably in the XY plane;
   a driving device for making the sample holder move in an X direction and in a Y direction independently in the XY plane;
   an position sensitive detector for detecting the travel in the X direction and in the Y direction; and
   a driving device for making the sample rotate in the XY plane perpendicular to the optical axis or in a slightly inclining plane;
   wherein a displacement of the optical axis of the optical system to the sample incident to a rotation of the sample corrects by making the sample holder move in the X direction and in the Y direction independently in the XY plane according to the angle θ by which the sample is rotated.

2. The charged particle beam equipment according to claim 1,
   wherein the sample holder that holds a sample of the charged particle beam equipment rotatably has a rotation detector for detecting the rotation angle θ of the sample.

3. The charged particle beam equipment according to claim 1,
   wherein the correction of a displacement of the sample to be put under observation or to machining incident to the sample rotation is executed based on:
   (1) detection of rotation center coordinates of a sample rotary mechanism;
   (2) detection of an optical-axis position to the sample; and
   (3) entry of the sample rotation angle θ and a rotation action according thereto, or detection of the rotation angle θ after actual rotation.

4. The charged particle beam equipment according to claim 1, further comprising a single or plurality of charged particle beam adjusting devices in addition to the sample holder.

5. The charged particle beam equipment according to claim 4,
   wherein rotation operations of all or selected several rotary mechanisms of these mechanisms and corrections of displacements from the optical axis incident to the rotation are performed while they are mutually interlocked, in each rotary mechanism of the charged particle beam equipment equipped with the sample holder and the single or plurality of charged particle beam adjusting devices.

6. The charged particle beam equipment according to claim 5,
   wherein interlocking of the sample holder and the rotary mechanism of the single or plurality of charged particle beam adjusting devices is executed based on:
   (1) detection of the rotation center coordinates of the each rotary mechanism;

(2) finalization of working conditions (magnification, focal length, etc.) of each lens of the optical system; and (3) calculation of a relative ratio of horizontal move distances of the rotary mechanisms under the optical conditions.

7. A charged particle beam equipment used for observation or machining of a sample, comprising:
a sample holder that holds the sample movably in an XY plane perpendicular to an optical axis of an optical system of the charged particle beam equipment or in a slightly inclining plane;
a driving device that holds a charged particle beam adjusting device rotatably in the XY plane perpendicular to the optical axis of the optical system of the charged particle beam equipment or in a slightly inclining plane and holds the charged particle beam adjusting device movably in the XY plane and that makes the charged particle beam adjusting device move in an X direction and in a Y direction independently in the XY plane;
a position sensitive detector for detecting the travel in the X direction and in the Y direction; and
a driving device for making the charged particle beam adjusting device rotate in the XY plane perpendicular to the optical axis or in a slightly inclining plane,
wherein a displacement of the optical axis of the optical system to the charged particle beam adjusting device incident to the rotation of the charged particle beam adjusting device corrects by making the charged particle beam adjusting device move in the X direction and in the Y direction independently in the XY plane according to the angle θ by which the charged particle beam adjusting device is rotated.

8. The charged particle beam equipment according to claim 7,
wherein the charged particle beam adjusting device of the charged particle beam equipment has a rotation detector for detecting the rotation angle θ of the charged particle beam adjusting device.

9. The charged particle beam equipment according to claim 7,
wherein the charged particle beam adjusting device signifies a single or plurality of devices or mechanisms that limit or alter an angular distribution and a spatial distribution of the charged particle beam on the charged particle beam optical system and are represented by a movable aperture, such as an objective aperture or selected area aperture.

10. The charged particle beam equipment according to claim 7,
Wherein the charged particle beam adjusting devices signifies a single or plurality of charged particle beam deflectors, such as a biprism.

11. The charged particle beam equipment according to claim 7,
wherein the charged particle beam adjusting device is constructed to be of a holder type and have a mechanism for facilitating mount/demount on/from the optical axis or mount/demount in/from a vacuum state of the charged particle beam equipment.

12. The charged particle beam equipment according to claim 7, execute
wherein correction of a displacement of the optical axis of the optical system to the electron beam adjusting device incident to the rotation of the electron biprism is executed based on:
(1) detection of rotation center coordinates of a rotary mechanism of the electron beam adjusting device;

(2) detection of an optical-axis position to the electron beam adjusting device; and
(3) entry of the rotation angle θ of the electron beam adjusting device and a rotation action according thereto, or detection of the rotation angle θ after actual rotation.

13. An electron microscope, having:
an electron beam source;
a light source that is made up by an electron beam emitted from the electron beam source through an irradiation optical system;
a sample holder that holds a sample and allows irradiation of the electron beam from the light source onto the sample;
an objective lens provided downstream of the sample holder;
an objective aperture provided downstream of the objective lens;
a first electron biprism provided downstream of the objective aperture;
a first selected area aperture provided in the same stage or downstream of the first electron biprism;
a first magnifying lens provided downstream of the selected area aperture;
a second electron biprism provided downstream of the first magnifying lens;
a second selected area aperture provided in the same stage or downstream of the second electron biprism;
a magnifying lens system disposed serially downstream of it;
an observation plane provided in the last stage of these imaging systems; and
a mechanism for allowing the operator to observe or recording this observation plane,
the electron microscope further comprising:
a driving device that holds the first or second or both of the electron biprism(s) movably in an XY plane perpendicular to an optical axis of an optical system of the electron microscope, and holds the one or the both rotatably in the XY plane or in a slightly inclining plane, and makes the first or second or the both of the electron biprism(s) move in an X direction and in a Y direction independently in the XY plane on which the one or the both are located; and
a position sensitive detector for detecting positions in the X direction and in the Y direction,
the electron microscope further having a driving device for making the each electron biprism rotate,
wherein a displacement of each optical axis of the optical system to the electron biprism incident to rotation of the each electron biprism corrects by making the each electron biprism move in the X direction and in the Y direction independently in the XY plane of the each.

14. The charged particle beam equipment according to claim 13,
wherein the each electron biprism of the electron microscope independently has a rotation detector for detecting the rotation angle θ of the each electron biprism.

15. The electron microscope according to claim 13,
wherein the objective lens is separated into two or more stages of lenses, which, as a whole, compose the objective lens, and the each objective lens can be controlled in terms of lens conditions, such as a focal length, independently.

16. The electron microscope according to claim 15,
wherein, in the objective lens system that is separated into two or more stages, all of, any one of, or any two of the objective aperture, the electron biprism, the selected area aperture are installed between the objective lenses sequentially along a flow direction of the electron beam, and the each of them can be controlled in terms of travel of position independently.

17. The electron microscope according to claim 16, wherein all or any one of the objective aperture, the electron biprism, and the selected area aperture installed between the objective lenses as divided into a plurality of stages can be controlled independently in terms of rotation.

18. The charged particle beam equipment according to claim 17, wherein the each rotary mechanism independently has a rotation detector for detecting the rotation angle θ.

19. The electron microscope according to claim 13, wherein correction of a displacement of the optical axis of the optical system to the electron biprism incident to the rotation of the electron biprism at each mechanism is executed based on:
(1) detection of rotation center coordinates of the rotary mechanism of the electron biprism;
(2) detection of an optical-axis position to the electron biprism; and
(3) entry of the rotation angle θ of the electron biprism and a rotation action according thereto, or detection of the rotation angle θ after actual rotation.

20. The electron microscope according to claim 19, wherein a rotation operation of the each rotary mechanism and the correction of a displacement from the optical axis incident to its rotation are performed while they are mutually interlocked, in all or some of the plurality of electron biprisms each equipped with a rotary mechanism.

21. The electron microscope according to claim 20, wherein interlocking of the rotary mechanisms of the plurality of electron biprisms each equipped with a rotary mechanism is executed based on:
(1) detection of the rotation center coordinates of the rotary mechanism of the electron biprism;
(2) finalization of working conditions of each lens of the optical system; and
(3) calculation of a relative ratio of horizontal move distances of the rotary mechanisms under the optical conditions.

22. An electron microscope, having:
an electron beam source;
a light source that is made up by an electron beam emitted from the electron beam source through an irradiation optical system;
a sample holder that holds a sample and allows irradiation of the electron beam from the light source onto the sample;
an objective lens provided downstream of the sample holder;
an objective aperture provided downstream of the objective lens;
a first selected area aperture provided downstream of the objective aperture;
a first magnifying lens provided downstream of the selected area aperture;
a magnifying lens system disposed serially downstream of it;
a observation plane provided in the last stage of these imaging systems; and
a mechanism for allowing the operator to observe or recording this observation plane;
the electron microscope further comprising:
a driving device that holds the sample holder movably in an XY plane perpendicular to the optical axis of the optical system of the electron microscope, holds the sample holder rotatably in the XY plane or in a slightly plane, and makes the sample holder move in an X direction and in a Y direction in the XY plane on which the sample holder is located independently; and
a position sensitive detector for detecting a position in the X direction and in the Y direction,
and the electron microscope still further including:
a driving device for rotating the sample holder,
wherein a displacement of the optical axis of the optical system to the sample holder incident to the rotation of the sample holder corrects by making the sample holder move in the X direction and in the Y direction independently in the XY plane of the each according to an angle θ by which the sample holder is rotated.

23. The electron microscope according to claim 22, wherein the sample holder of the electron microscope has a rotation detector for detecting the rotation angle θ of the sample holder.

24. The electron microscope according to claim 22, wherein correction of a displacement of the optical-axis of the optical system to the sample holder incident to the rotation of the sample holder is executed based on:
(1) detection of rotation center coordinates of the rotary mechanism of the sample holder;
(2) detection of an optical-axis position to the sample holder; and
(3) entry of the rotation angle θ of the sample holder and a rotation action according thereto, or detection of the rotation angle θ after actual rotation.

* * * * *